United States Patent [19]
Rijke et al.

[11] Patent Number: 5,462,068
[45] Date of Patent: Oct. 31, 1995

[54] WRIST FIXATION DEVICE FOR ELBOW STRESS EXAMINATION

[75] Inventors: Arie M. Rijke, Charlottesville, Va.; Henry T. Goitz, St. Clair Shore, Mich.

[73] Assignee: University of Virginia Patent Foundation, Charlottesville, Va.

[21] Appl. No.: 19,602

[22] Filed: Feb. 19, 1993

[51] Int. Cl.⁶ ........................................................ H05G 1/00
[52] U.S. Cl. ............................ 128/881; 378/178; 128/878
[58] Field of Search .................................... 128/774, 782, 128/877, 878, 879, 881, 882; 378/178, 179, 180, 208

[56] References Cited

U.S. PATENT DOCUMENTS

| | | | |
|---|---|---|---|
| 4,407,277 | 10/1983 | Ellison | 378/208 |
| 4,674,110 | 6/1987 | Eaton | 378/180 |
| 5,275,174 | 1/1994 | Cook | 128/782 |

FOREIGN PATENT DOCUMENTS

| | | | |
|---|---|---|---|
| 2156225 | 10/1985 | United Kingdom | 128/878 |

Primary Examiner—Michael A. Brown
Assistant Examiner—David J. Kenealy
Attorney, Agent, or Firm—Sheldon H. Parker

[57] ABSTRACT

The device is a diagnostic tool for the determination of the functional loss of the collateral ligaments of the elbow. The device serves to position and to stabilize the arm of a subject and to position the elbow in a predetermined fixed position to allow for X-raying of elbow joints under graded pressure. A first part of the device is a unit for receiving a hand and securing the wrist in a predetermined position. The hand receiving member has a planar upright support section which has a plurality of spaced holes. Preferably, the spaced holes are arranged in a plurality of parallel rows. The first part includes a first rod shaped member or roller positioned in a hole such that it is contacted by the palm of the hand, with the palm upward in supination. The wrist is secured to a second rod or roller mounted in another of the holes, to hold the wrist in a predetermined position relative to the second roller. A third roller is provided such that the wrist is locked in position between the second and third rollers. Each of the plurality of hand securing rollers are positionable in the spaced holes so as to be adjustable relative to each other so as to receive a hand and wrist and to secure the hand and wrist in a predetermined supination position. A vertical post is provided for bracing the shoulder and a pressure mechanism applies pressure to the radiohumeral joint to elicit widening of the medial joint space.

16 Claims, 5 Drawing Sheets

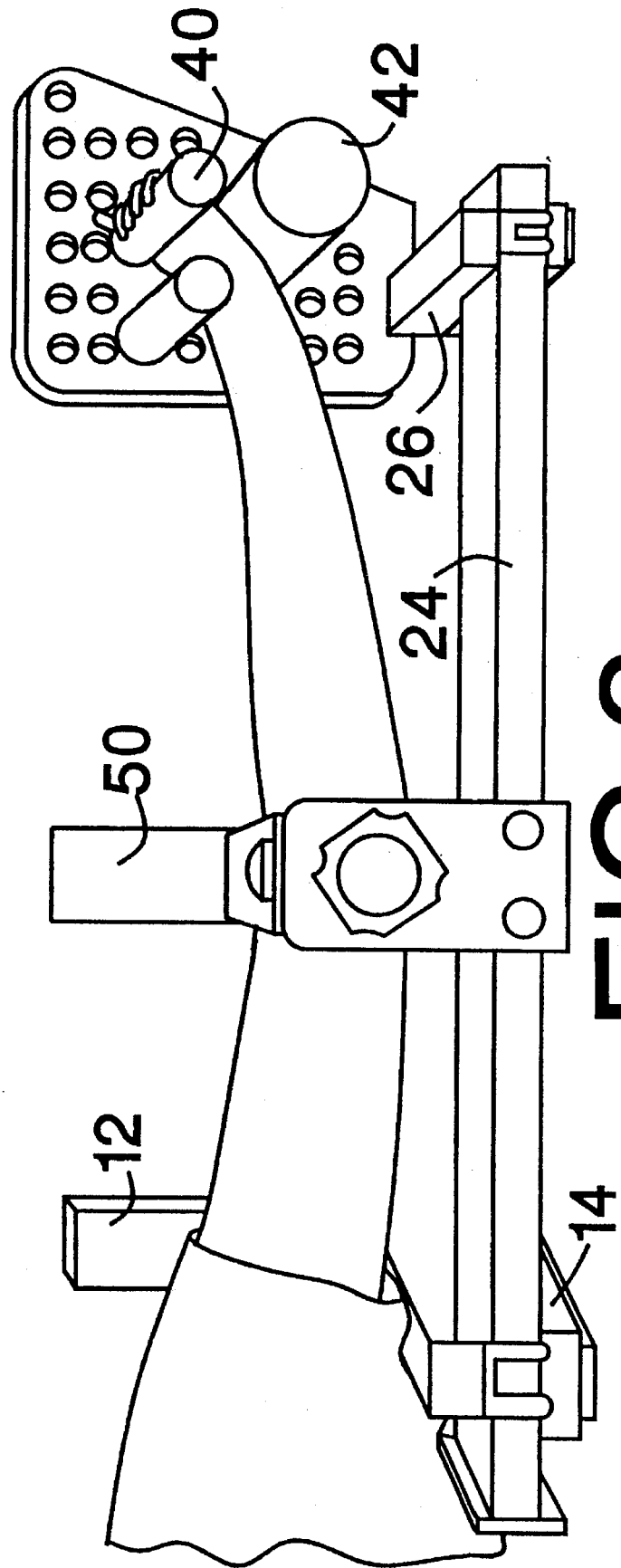

WRIST FIXATION DEVICE FOR ELBOW STRESS EXAMINATION

FIELD OF THE INVENTION

This invention relates generally to devices for securing and stabilizing the wrist in supination, for stress examination of the elbow ligaments.

BRIEF DESCRIPTION OF THE PRIOR ART

Sports injuries can be very painful and debilitating. Not all injuries, however, require surgery and many ligament injuries can be healed through rest and physical therapy. Determining the extent of the damage to ligaments allows the physician to evaluate whether or not surgery is required. The typical methods for evaluating damage to ligaments are magnetic resonance imaging (MRI), computerized axial tomography (CAT) scan and x-ray radiography. CT arthography relies on the presumed association of capsular extravasation of contrast with collateral ligament rupture. This method is unexplored and it is unknown whether reliable, consistent results can be obtained. Although MRI can directly image the affected ligament, it is unable to assess function properties. Both CT arthography and MRI techniques are high-cost and do not provide the reliability of the instant invention.

Devices are known for stabilizing a limb of the body for examination. As for example, U.S. Pat. No. 5,136,743 to Pirela-Cruz discloses a device for positioning the distal radiohumal joint (DRUJ) for medical examination. The Pirela-Cruz device allows stress to be applied to the radius and ulna to assess stability in the DRUJ and is especially useful for a CAT scan or X-rays.

U.S. Pat. No. 4,969,471 to Daniel et al., discloses a device which simultaneously measures mutually perpendicular linear displacements and angular displacements about an axis substantially perpendicular to the plane off the linear of the linear displacements. The Daniel et al device is particularly designed for use in connection with knee injuries.

U.S. Pat. No. 5,163,443 to Fry-Welch et al measures the forces which are applied by a limb and is useful for determining the presence of cumulative trauma disorders, such as carpal tunnel syndrome.

U.S. Pat. No. 3,715,587 to Burkhalter et al discloses instruments for performing in vivo analysis of bone mineral content by measuring the absorption of a scanning beam of monoenergetic photons.

The foregoing patents illustrated that there is a need for various devices to position limbs during analysis of injuries, as well as techniques to evaluate the injury. None of the prior art have addressed the problem of X-raying boney structures to reliably and reproducibly predict injury to ligaments. In the instant invention the extent of the injury can be quantitated non-invasively, particularly in the elbow area.

BRIEF DESCRIPTION OF THE DRAWING

FIG. 6 is a side view of the instant invention of FIG. 1 in use.

SUMMARY OF THE INVENTION

Figure 1:
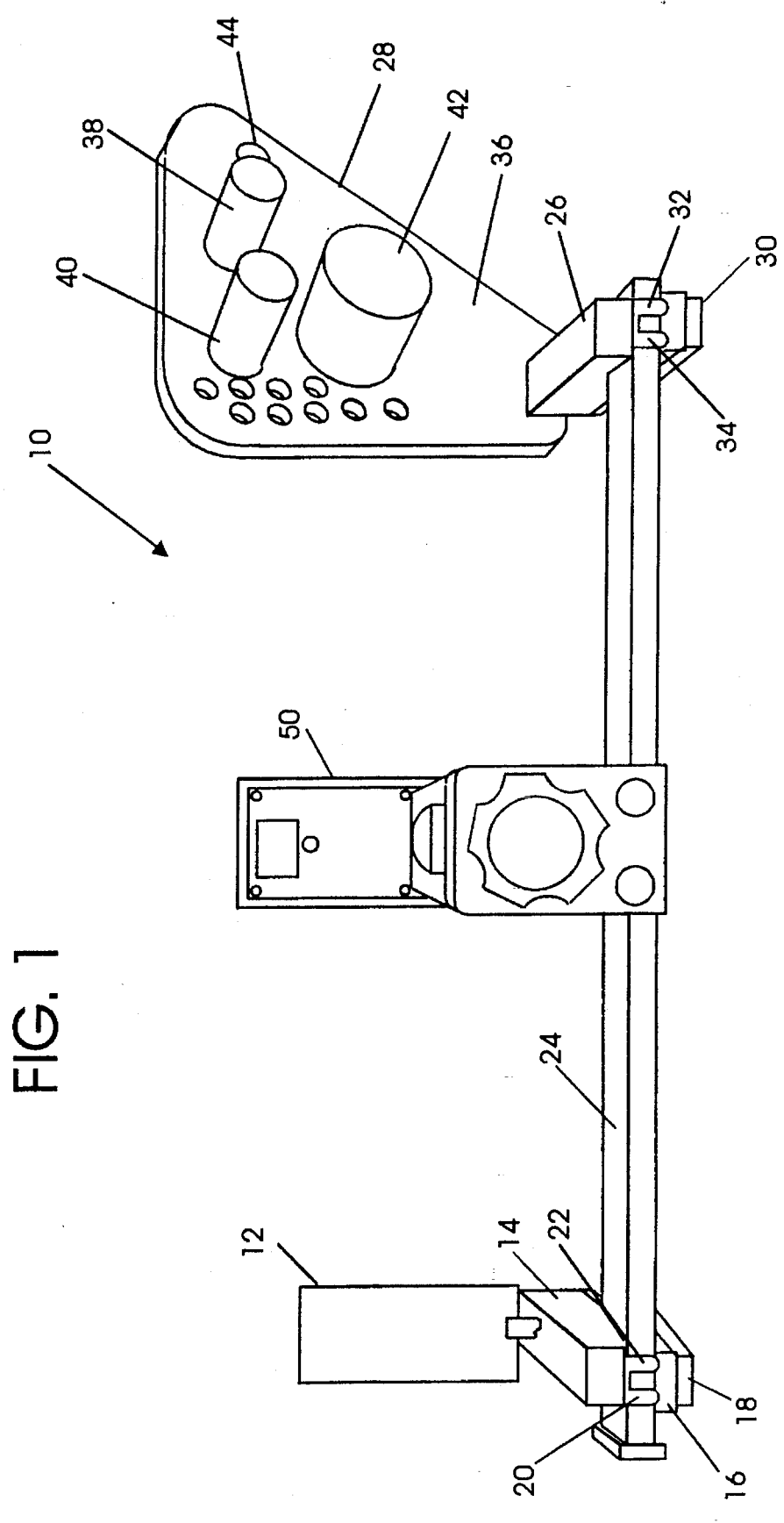
FIG. 1 is a side view of the instant invention.

A device of the present invention is employed as a diagnostic tool for the determination of the functional loss of the collateral ligaments of the elbow. The device serves to position and stabilize the arm of a subject and to position the elbow in a predetermined fixed position to allow for X-raying of the elbow under graded pressure.

A first part of the device is a unit for receiving a hand and securing the wrist in a predetermined position. The hand receiving member has a planar upright support section which has a plurality of spaced holes, preferably in a plurality of parallel rows. The first part includes a first rod shaped member or roller positioned in a hole such that it is contacted by the palm of the hand, with the palm upward in a supine position. The wrist is secured to a second rod or roller mounted in another of the holes, to hold the wrist in a predetermined position relative to the second roller. In a preferred embodiment, a third roller is provided and the wrist is locked in position between the second and third rollers. Each of the roller members are dimensioned to be received in the spaced holes, such that they extend from the support section parallel to each other. The three rollers are located in the holes of the support member such that they are positioned at the apices of a triangle. Each roller has a resilient, tubular element enclosing at least a major portion of its length. Each of the plurality of hand securing rollers are positionable in the spaced holes so as to be adjustable relative to each other so as to receive a hand and wrist and to secure the hand and wrist in a predetermined supine position.

A second part of the device is a vertical post against which the shoulder is braced. The shoulder brace is rotatably supported on the carrier member, such that it is rotatably adjustable about a vertical axis.

A third part is a mechanism for applying pressure to the radiohumeral joint to elicit widening of the joint space. The third part is provided with a rotatable, threaded shaft. Rotation of the shaft causes a vertical portion of the third part to move relative to the elbow, thereby varying the degree of force being applied to the elbow. Also provided, is a device for reading the degree of force being applied to the joint. The third part is supported for movement normal to an imaginary first plane which includes the first and second parts of the device. By applying pressure to the radiohumeral joint widening of the medial elbow joint space is elicited.

The first part and the second part are positioned on the same side of the arm and the third part is positioned on the opposite side of the arm, such that movement of the third means in a direction normal to the first plane varies the pressure to the radiohumeral joint.

A carrier member is provided for adjustably retaining the first, second and third parts of the device. The carrier member is an elongated support element on which the three parts move relative to each other. Thus, the hand receiving member, the shoulder brace and the pressure mechanism are adjustably retained on the carrier member, and are spatially adjustable relative to each other to accommodate various arm lengths.

The procedure of the invention involves the determination of the functional loss of the collateral ligaments of the elbow, by (a) securing the wrist in a predetermined position, and maintaining the hand in a fixed position, (b) bracing the shoulder against movement in a first direction, (c) applying pressure in the first direction to the radiohumeral joint to elicit widening of the medial joint space while maintaining a predetermined flexion of elbow, and (d) X-raying of boney structures of the elbow under graded pressure.

Preferably, the flexion of the elbow is on the order of about 25°.

In step (c) the pressure is applied in increments to the radiohumeral joint and in step (d) the incremental widening of the medial joint space is recorded by means of X-raying of the joint. The functional loss of the collateral ligaments of the elbow is based on the relationship between the widening and the applied pressures.

DETAILED DESCRIPTION OF THE INVENTION

The instant invention discloses a device which allows for the elbow to be placed in a fixed position to allow for ligament X-rays under graded pressure. Increased pressure is applied to the radiohumeral joint to elicit widening of the medial joint space, with each increment of pressure being recorded on X-ray film. Recording the widening of the medial joint space allows for the determination of the functional loss of the collateral ligaments of the elbow based on the relationship between the widening and the applied pressures. By way of contrast, prior diagnostic systems were restricted to the gravity valgus test, that used the weight of the forearm to provoke ulnohumeral subluxation.

The wrist fixation device of the present invention stabilizes the wrist in supination, a requirement for stress examination of the elbow ligaments. The device includes a vertical, planar member which supports a plurality of foam rubber covered roller bars in a variety of relative positions. The fingers clasp the distal roller bar, such that the volar aspect of the wrist is secured to the proximal roller bar by Velcro straps 62 of FIG. 6, or other means, or otherwise held in a fixed position, as for example, further roller bars.

FIG. 1 illustrates a side view of the positioning device 10. The shoulder brace 12 is affixed at right angles to the slide brace 14 and provides the "set point" for positioning the arm. The shoulder brace 12 can be manufactured to slide within the slide brace 14, however little benefit would be derived from this as the positioning device 10 inherently allows for variations in arm size. The slide brace 14 is manufactured with a notched area dimensioned to receive the slide bar 24. Pegs 20 and 22 lock the slide bar 24 into the notched portion of the slide brace 14. A non-slip rubber base 18 prevents the positioning device 10 from moving while in use. A second slide brace 26 maintains the other end of the slide bar 24 parallel, with the slide bar 24 being locked into position within second slide brace through use of pegs 32 and 34. The slide brace 26 also has a non-slip rubber base 30. An adjustable pressure unit 50 is slidably mounted on the slide bar 24 to allow for accurate positioning of the pressure unit 50 over the radiohumeral joint. The slide braces 14 and 26, slide bar 24 and the pressure unit 50 are manufactured by Telos Company and have been used for cruciate ligament testing.

The adjustable wrist fixation panel 28 is affixed to the slide brace 26, on the same plane as the shoulder brace 12. The adjustable wrist fixation panel 28 illustrated herein is a trapezoidal shape, however this is a preferred configuration and should not be considered to limit the instant disclosure. The narrow portion of the adjustable wrist fixation panel 28 is affixed to the slide brace 26. The adjustable wrist fixation panel 28 is predrilled with parallel rows of receiving holes 44 to provide for adjustability. The distal roller bar 38 is a foam covered roller bar which has one end dimensioned to fit through the receiving holes 44 and lock into the adjustable wrist fixation panel 28. The proximal roller bar 40 is manufactured identical to the distal roller bar 38 and is also locked into the adjustable wrist fixation panel 28. The distal roller bar 38 and the proximal roller bar 40 are interchangeable from a manufacturing purpose, however they have been referred to separately herein for clarification. The distal roller bar 38 and proximal roller bar 40 are positioned on the adjustable wrist fixation panel 28, in conjunction with the wrist brace 42, to lock the wrist in supination. The ability to keep the wrist in a supination is critical so that a reproducible anterior-posterior position of the elbow with respect to the direction of the X-ray beam is maintained and rotation is avoided. The reproducibility of the positioning of the elbow, in essence, means that a desired predetermined position of the elbow will be attained through the method and apparatus of the invention. In addition, wrist supination is thought to help decrease muscle splintering by the flexor capri ulnaris-radialis muscles.

As illustrated in FIG. 6, the patient's shoulder is placed against the shoulder brace 12 with the elbow flexed 25° and resting on or near the x-ray film cassette. The wrist is placed to rest on the wrist brace 42 and the proximal roller bar 40 is positioned at the volar portion of the wrist to lock the wrist in the desired position. The distal roller bar 38 is positioned to allow the patient's fingers to close around the distal roller bar 38. The receiving holes 44 allow for the distal roller bar 38, proximal roller bar 40 and the wrist brace 42 to be positioned to maintain a 25° flexion of the elbow so as to unlock the humeral-olecranon joint. The pressure unit 50 is placed adjacent to the radiohumeral joint and pressure is applied to the joint, as shown in FIG. 2.

Figure 2:
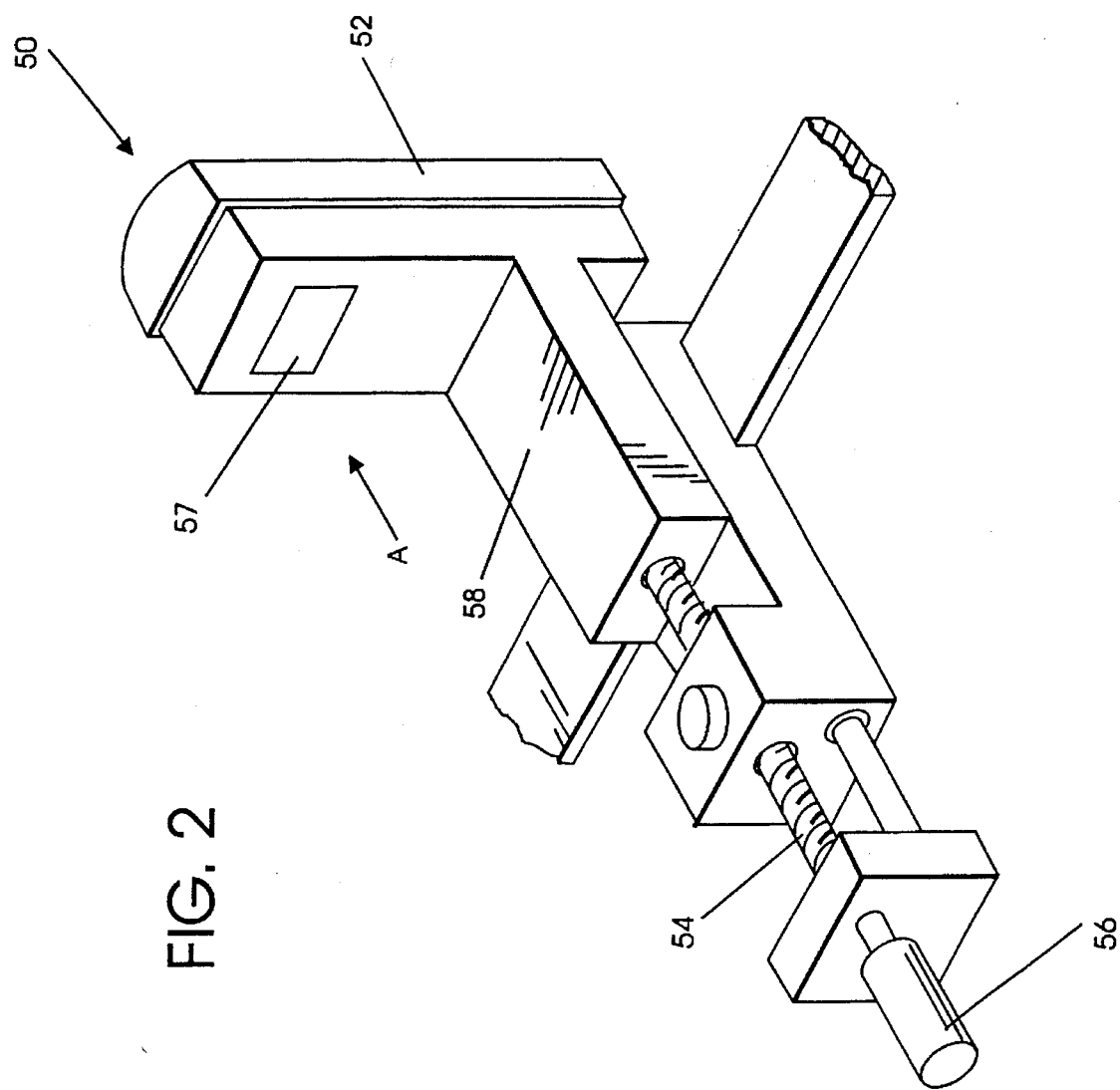
FIG. 2 is a perspective view of the instant invention in use.

FIG. 2 illustrates the pressure unit 50 in a position to apply pressure to the radiohumeral joint. The threaded screw 54 extends through the pressure unit 50 and has a rotatable handle 56 at one end and is connected to the pressure panel base 58 at the other end. As the rotatable handle 56 is turned in one direction, the threaded screw 54 is removed from the pressure panel base 58, forcing the pressure panel base 58 in the direction of Arrow A. The pressure panel 52 is in contact with the patient's elbow prior to the application of pressure. As the pressure panel base 58 extends toward the patient's elbow, pressure is applied through the pressure panel 52 to the radiohumeral joint. A digital numeral display 57 indicates the amount of pressure applied to the joint. After each increased increment of pressure, an x-ray is taken of the joint.

Figure 3:
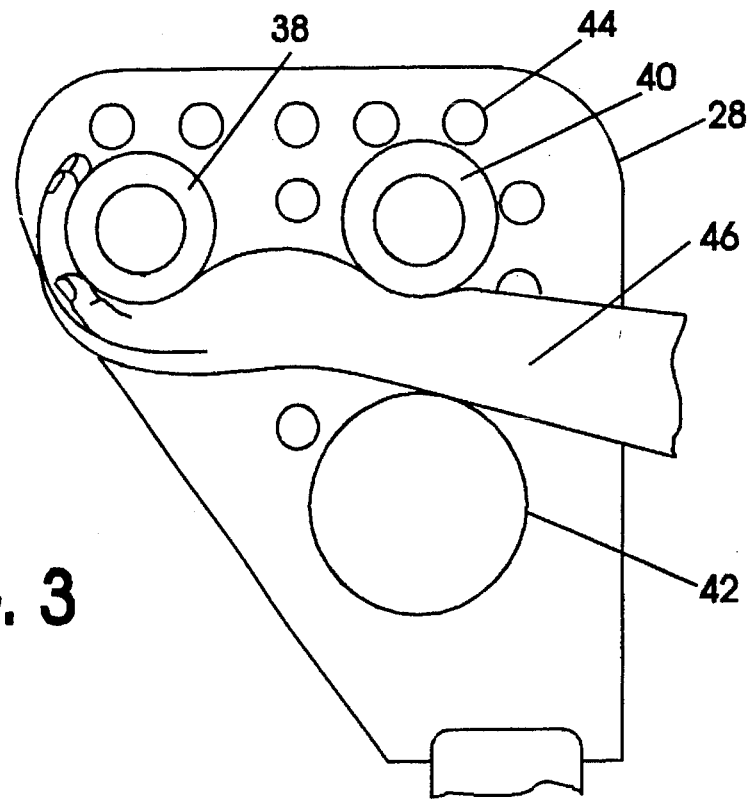
FIG. 3 is a side view of the adjustable panel of the instant invention.

FIG. 3 illustrates a detailed view of the adjustable wrist fixation panel 28 with the distal roller bar 38, proximal roller bar 40 and wrist brace 42 inserted into the receiving holes 44. The patient's arm 46 has been placed in the appropriate position for examination. The receiving holes 44 are predrilled into the adjustable wrist fixation panel 28 in a predetermined, desired pattern. The patient's hand grips the distal roller bar 38 and the proximal roller bar 40 and wrist brace 42 lock the forearm in a position to maintain the wrist in supination. In the illustration herein, the receiving holes 44 are drilled in rows of varying length. This is presented as an example of the configuration and should not be considered as a limitation. It is critical, however, that a sufficient number of receiving holes 44 be provided to allow for maximum adjustability. As an alternative to use of the proximal roller bar 40, the wrist brace 42 can be provided with Velcro® straps to affix the wrist in place.

Figure 5:
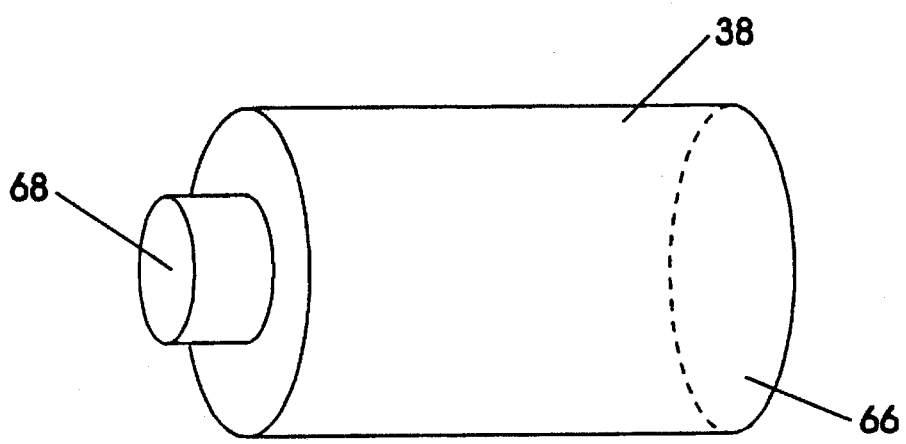
FIG. 5 is a perspective view of the grips of the instant invention.
Figure 4:
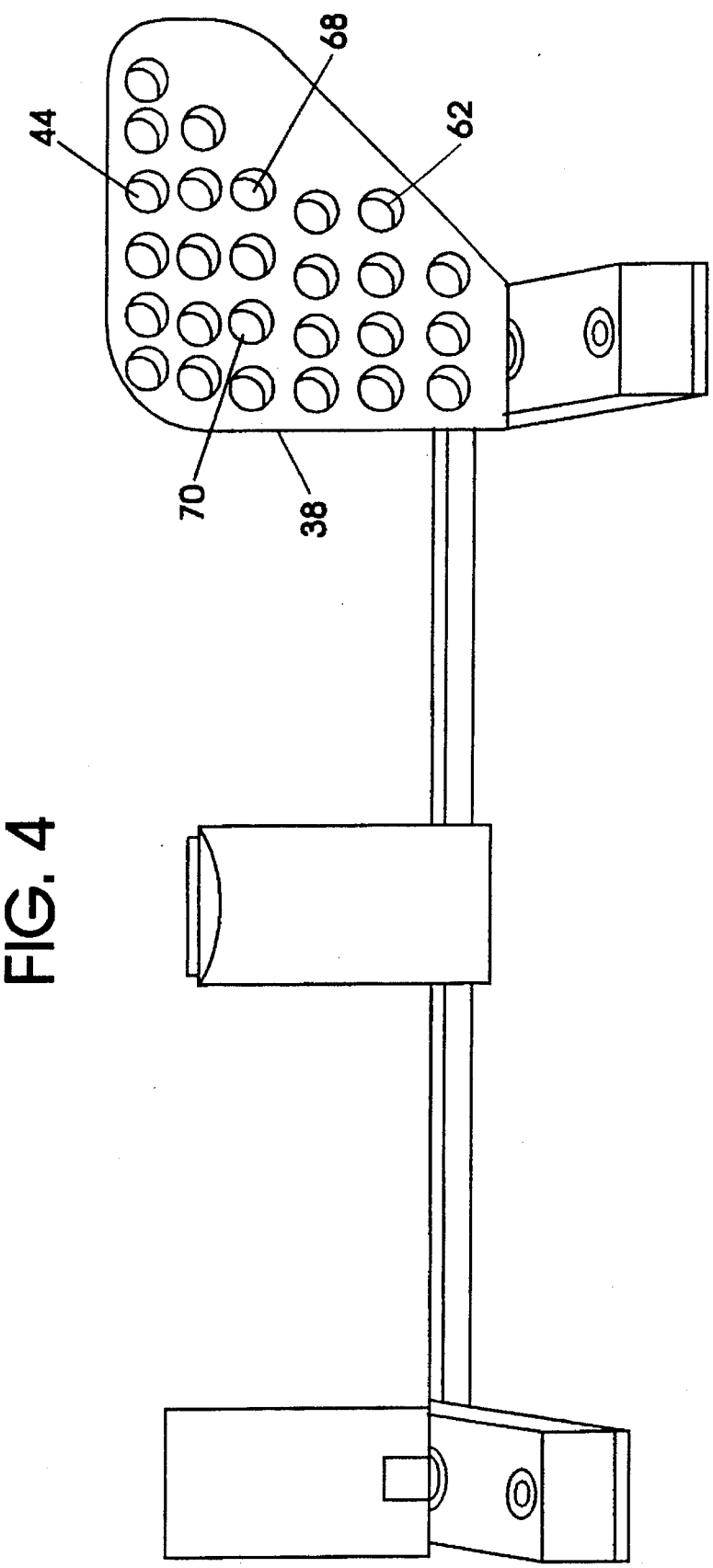
FIG. 4 is a side view of the reverse side of FIG. 1.

FIG. 4 illustrates the reversed side of FIG. 1, illustrating one method of inserting the distal roller bar 38, proximal roller bar 40 and wrist brace 42. The distal roller bar 38, illustrated in FIG. 5, is a foam covered bar 68 which extends beyond the foam 66. The bar 68 is dimensioned for a friction fit into the receiving holes 44. As an alternative design, the portion of the bar 68 covered by foam 66 can have an increased diameter. The portion of the bar 68 which extends into the receiving holes 44 should be approximately equal to the depth of the receiving holes 44 to prevent tilting or breakage when pressure is applied. Various additional methods known to those versed in the prior art can be used to lock the bar 68 into the adjustable wrist fixation panel 28.

What is claimed is:

1. A device for use in the evaluation of the medial elbow ligaments by positioning and stabilizing the hand, arm and shoulder of a subject, thereby positioning the elbow in a predetermined fixed position to allow for X-raying the elbow under graded pressure, comprising:

(a) a slide brace, said slide brace having a first end, a second end, a predetermined length and attachment means along said length, (b) a vertical wrist fixation panel for receiving a patient's hand and wrist and securing the wrist in a predetermined position, said panel being slidably positioned proximate said first end of said slide brace and including:
       a first roller positioned to be contacted by the palm of the hand,
       a second roller, and
       wrist securing means to hold said wrist in a predetermined position relative to said second roller, (c) a shoulder brace for contacting the shoulder, said shoulder brace being slidably positioned proximate said second end of said slide brace, and (d) pressure means for applying pressure to the radiohumeral joint to elicit widening of the medial joint space, said pressure means being slidably affixed to said slide brace, wherein said panel, shoulder brace and pressure means are at approximately right angles to said slide brace.

2. The device of claim 1, wherein said panel further comprising a third roller positioned and spaced relative to said second roller to receive and secure the wrist.

3. The device of claim 2, wherein said panel and said shoulder brace are positioned to be in contact with a first side of the arm and said pressure means is positioned to be in contact with the opposite side of the arm, such that movement of said pressure means in a direction normal to said first side of the arm varies the pressure to the radiohumeral joint.

4. A device for the determination of the functional loss of the collateral ligaments of the elbow, comprising:

(a) a hand receiving member, said hand receiving member having
       a planar upright support member, said support member having a plurality of spaced holes,
       a plurality of hand securing members, each of said hand securing members being dimensioned to be received in said spaced holes, and being positioned in said spaced holes in a pattern to support and secure a hand and wrist in a predetermined position, (b) a shoulder brace for contacting the shoulder, said shoulder brace being an upright member, said hand receiving member and said shoulder brace lying substantially in a first plane, (c) pressure means for applying pressure to the radiohumeral joint to elicit widening of the medial joint space, said pressure means being an upright member supported for movement normal to said first plane, and (d) an elongated carrier member, each of said hand receiving member, said shoulder brace and said pressure means being adjustably retained on, and substantially at right angles to, said carrier member, whereby each of said hand receiving member, said shoulder brace and said pressure means are spatially adjustable relative to each other, along said carrier member, to accommodate various arm lengths.

5. The device of claim 4, wherein said shoulder brace is a substantially planar member and further comprises means for rotatably supporting said shoulder brace on said carrier member, thereby allowing said shoulder brace to be rotatably adjustable while remaining at right angles to said carrier member and remaining in said first plane.

6. The device of claim 4, wherein said spaced holes in said planar upright support member are in a plurality of spaced parallel rows.

7. The device of claim 4, wherein said each of said hand securing members is a rod shaped element having a tubular resilient cover member.

8. The device of claim 7, wherein the axis each of rod shaped element, when placed in said spaced holes, is substantially parallel to each other.

9. The device of claim 8, wherein said hand securing members include a palm receiving member and a pair of wrist securing members, said pair of wrist securing members being positionable on substantially opposite sides of a patient's wrist, said palm receiving member and said pair of wrist securing members being at the vertexes of a triangle, thereby fixing the wrist in a predetermined position.

10. The device of claim 4, further comprising means for retaining said hand receiving member in any one of a plurality of fixed positions along said carrier member.

11. The device of claim 4, wherein said pressure means is adjustably supported on said carrier member between said shoulder means and said hand receiving member, whereby the position of said pressure means on said carrier member is adjustable relative to said hand receiving member and said shoulder means, thereby providing for the accommodation of arms of differing dimensions.

12. The device of claim 4, wherein said pressure means comprises:

a resilient pad member, said resilient pad member being positioned on the outer surface of said pressure means, thereby providing for cushioned contact with an elbow,
    a rotatable, threaded shaft means, and
    moving means, said moving means connecting said pressure means and said shaft means and responding to the rotation of said threaded shaft means by moving said pad member in a direction normal to the major axis of said elongated support element, thereby applying or releasing graded pressure to the radiohumeral joint.

13. The method of determination of the functional loss of the collateral ligaments of the elbow, using a device having:

(a) a hand receiving member, said hand receiving member having
       a planar upright support member, said support member having a plurality of spaced holes, a plurality of hand securing members, each of said hand securing members being dimensioned to be received in said spaced holes and positionable in said planar upright support member to receive a hand and wrist and to secure said hand and wrist in a predetermined position, (b) a shoulder brace for contacting the shoulder, said shoulder brace being an upright member, said hand receiving member and said shoulder brace lying substantially in a first plane, (c) pressure means for applying pressure to the radiohumeral joint to elicit widening of the medial joint space, said pressure means being an upright member supported for movement normal to said first plane, and (d) an elongated carrier member, each of said hand receiving member, said shoulder brace and said pressure means being adjustably retained on said carrier member, each of said hand receiving member, said shoulder brace and said pressure means are spatially adjustable relative to each other, along said carrier member, to accommodate various arm lengths;

comprising the steps of:

(i) determining the optimum elbow flexion for the individual patient, (ii) placing the first of said hand securing members in one of said plurality of spaced holes positioned to maintain said optimum flexion, (iii) placing the remaining hand securing members in said plurality of spaced holes to secure the wrist and hand in a position to maintain said optimum flexion, (iv) bracing the shoulder against said shoulder brace, thereby blocking horizontal movement in one direction, (v) applying pressure by said pressure means in said one direction to the radiohumeral joint to elicit widening of the medial joint space while maintaining said optimum flexion of elbow, and (vi) X-raying of the elbow under graded pressure.

14. The method of claim 13, wherein said optimum flexion is on the order of about 25°.

15. The method of claim 13, wherein step (v) comprises applying increments of pressure to the radiohumeral joint and step (vi) comprises the recording of the incremental widening of the medial joint space, whereby the determining of the functional loss of the collateral ligaments of the elbow is based on the relationship between the widening and the applied pressures.

16. The method of claim 15, wherein the patient's arm is placed in said device with the palm facing upward in supination, the fingers grasping a first hand securing members, and the wrist secured in a predetermined position between a second and a third hand securing member.

* * * * *